(12) United States Patent
Keri et al.

(10) Patent No.: US 6,734,314 B2
(45) Date of Patent: May 11, 2004

(54) PREPARATION OF ORLISTAT AND ORLISTAT CRYSTALLINE FORMS

(75) Inventors: Vilmos Keri, Debrecen (HU); Andrea Csorvasi, Debrecen (HU); Judith Aronhime, Rehovot (IL)

(73) Assignee: Biogal Gyogyszergyar Rt., Debrecen (HU)

( * ) Notice: Subject to any disclaimer, the term of this patent is extended or adjusted under 35 U.S.C. 154(b) by 0 days.

(21) Appl. No.: 10/313,601

(22) Filed: Dec. 4, 2002

(65) Prior Publication Data

US 2003/0149095 A1 Aug. 7, 2003

Related U.S. Application Data

(60) Provisional application No. 60/337,218, filed on Dec. 4, 2001.

(51) Int. Cl.[7] .............................................. C07D 305/12
(52) U.S. Cl. ...................... 549/328; 549/263; 435/123
(58) Field of Search ................................ 549/328, 263; 435/123

(56) References Cited

U.S. PATENT DOCUMENTS

| | | | |
|---|---|---|---|
| 4,598,089 A | 7/1986 | Hadvary et al. | 514/449 |
| 4,983,746 A | 1/1991 | Barbier et al. | 549/328 |
| 5,200,526 A | 4/1993 | Arnold et al. | 548/375.1 |
| 5,902,886 A | 5/1999 | Schick et al. | 549/328 |
| 6,156,911 A | 12/2000 | Doswald et al. | 549/328 |

FOREIGN PATENT DOCUMENTS

| | | |
|---|---|---|
| EP | 0 129 748 A1 B1 | 1/1985 |
| EP | 0 638 317 A1 B1 | 2/1995 |

*Primary Examiner*—Ba K. Trinh
(74) *Attorney, Agent, or Firm*—Kenyon & Kenyon

(57) ABSTRACT

The present invention is directed to a process of converting lipstatin to orlistat by catalytic hydrogenation. The present invention further discloses novel crystalline solid orlistat forms, designated form I and form II and methods for their preparation.

37 Claims, 2 Drawing Sheets

PREPARATION OF ORLISTAT AND ORLISTAT CRYSTALLINE FORMS

CROSS-REFERENCE TO RELATED APPLICATION

This application claims the benefit under 35 U.S.C. § 1.119(e) of Provisional Application Ser. No. 60/337,218 filed Dec. 4, 2001, the disclosure of which is incorporated by reference in its entirety herein.

FIELD OF THE INVENTION

The present invention relates to a method of converting lipstatin to orlistat. The present invention also relates to crystalline solid orlistat (e.g., form I and form II).

BACKGROUND OF THE INVENTION

Orlistat is currently available for the treatment of obesity. It has the chemical name (2S, 3S, 5S)-5-[(S)-2-formamido-4-methylvaleryloxy]-2-hexy-3-hydroxyhexadecanoic acid lactone [a/k/a "N-formyl-L-leucine ester with (3S, 4S)-3-hexyl-4-[(2S)-2-hydroxytridecyl]-2-oxetanone", (-)-tetrahydrolipstatin, tetrahydrolipstatin, and orlipastat] and its chemical formula is:

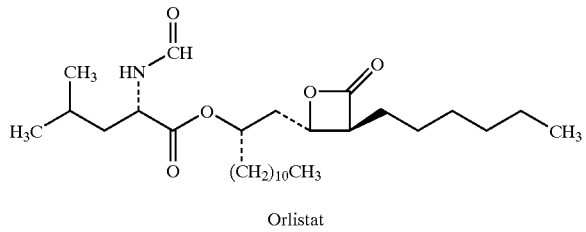

Orlistat

Orlistat has been purified from a fermentation broth of *Streptomyces toxytricini* (See U.S. Pat. No. 4,598,089 and Eur. Pat. Appl. 129,748). U.S. Pat. No. 4,598,089 is directed to orlistat and its use in treating obesity. The cultivation, fermentation and purification of orlistat produced in *Streptomyces toxytricini* were disclosed. The process involves purifying orlistat using a silica gel chromatography. The desired orlistat may then be subjected to further purification with a reverse-phase chromatography; thus, multiple chromatographies are required. The repeated purification processes is costly and impractical for large scale manufacturing.

U.S. Pat. No. 4,983,746 relates to a process for the artificial synthesis of orlistat which involves producing oxetanone derivatives; and esterification of the acid derivatives with an alcohol. The disadvantage of artificially synthesizing orlistat is its high cost, especially with industrial scale production.

EP 638317 describes a pharmaceutical composition including orlistat. However, there is no disclosure regarding the production and purification of orlistat. Such obtained orlistat is not desirable for preparing a pharmaceutical composition as it requires high purity.

There is a continuous need to improve the preparation of orlistat.

The present invention also relates to the solid state physical properties of orlistat. These properties can be influenced by controlling the conditions under which orlistat is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are determined by the conformation and orientation of molecules in the unit cell, which defines a particular polymorphic form of a substance. A particular crystalline form may also give rise to distinct spectroscopic properties that may be detectable by powder X-ray crystallography, or other parameters including solid state $^{13}C$ NMR spectrometry and infrared spectrometry. The polymorphic form may also give rise to thermal behavior different from that of the amorphous material or another crystalline form. Thermal behavior is measured in the laboratory by such techniques as capillary melting point, thermogravimetric analysis (TGA) and differential scanning calorimetry (DSC) and can be used to distinguish some polymorphic forms from others.

SUMMARY OF THE INVENTION

The present invention provides a process of preparing orlistat, comprising the steps of hydrogenating lipstatin in an organic solvent in the presence of a catalyst to obtain orlistat. Preferably, the organic solvent is selected from the group consisting of acetonitrile, alcohol, and acetone. Most preferably, the organic solvents are methanol and acetone.

Preferably, the catalyst is selected from the group consisting of palladium and nickel. Preferably, the hydrogenating step is performed at a temperature between about 10° C. to about 50° C. Preferably, the hydrogenating step is performed at reaction pressure of less than 5 bar. More preferably, the hydrogenating step is performed at reaction pressure between about 1 to about 3 bar. Most preferably, the hydrogenating step is performed at reaction pressure of about 1 bar.

The present invention provides a crystalline solid orlistat, or hydrate or solvate thereof, characterized by data selected from the group consisting of a XRD pattern with peaks at 5.8, 18.5, 19.5 and 22.3±0.2 degrees two-theta and a DSC melting endotherm at about 46.7° C.

Preferably, the crystalline solid orlistat is characterized by a XRD pattern with peaks at 5.8, 18.5, 19.5 and 22.3±0.2 degrees two-theta.

Preferably, the crystalline solid orlistat is further characterized by a XRD pattern substantially as depicted in FIG. 1.

Preferably, the crystalline solid orlistat characterized by a DSC melting endotherm at about 46.7° C.

The present invention provides a crystalline solid orlistat, or hydrate or solvate thereof, characterized by data selected from the group consisting of a XRD pattern with peaks at 4.8, 5.6, 14.9, 17.3, 19.2 and 22.0±0.2 degrees two-theta, and a DSC melting endotherm at about 46.6° C.

Preferably, the crystalline solid orlistat is characterized by a XRD pattern with peaks at 4.8, 5.6, 14.9, 17.3, 19.2 and 22.0±0.2 degrees two-theta.

Preferably, the crystalline solid orlistat is further characterized by a XRD pattern substantially as depicted in FIG. 2.

Preferably, the crystalline solid orlistat is characterized by a DSC melting endotherm at about 46.6° C.

The present invention provides a process of preparing crystalline solid orlistat, or hydrate or solvate thereof, characterized by data selected from the group consisting of a XRD pattern with peaks at 5.8, 18.5, 19.5 and 22.3±0.2 degrees two-theta and a DSC melting endotherm at about 46.7° C., comprising the steps of:

(a) dissolving orlistat in a solvent;

(b) adding an anti-solvent or water to the solvent; and (c) isolating the crystalline solid orlistat.

Preferably, the solvent is a lower alkyl alcohol, acetone, acetonitrile, acetone, ethyl acetate, isobutyl acetate, methyl isobutyl ketone, and hexane.

Preferably, the lower alkyl alcohol is selected from the group consisting of methanol, ethanol, n-propanol, and isopropanol. Preferably, the anti-solvent is a hydrocarbon. More preferably, the hydrocarbon is selected from the group consisting of hexane, cyclohexane and heptane. Most preferably, the solvent is methanol and the anti-solvent is hexane. Preferably, the steps (a) to (c) are repeated at least once to increase the purity of the crystalline solid orlistat.

The present invention provides the crystalline solid orlistat prepared in accordance with the process comprising the steps of:

(a) dissolving orlistat in a solvent;

(b) adding an anti-solvent or water to the solvent; and (c) isolating the crystalline solid orlistat.

The present invention provides a process for preparing a crystalline solid orlistat, or hydrate or solvate thereof, characterized by data selected from the group consisting of a XRD pattern with peaks at 4.8, 5.6, 14.9, 17.3, 19.2 and 22.0±0.2 degrees two-theta, and a DSC melting endotherm at about 46.6° C., comprising the steps of:

(a) mixing orlistat in hexane to form a mixture at a first temperature;

(b) lowering the first temperature of the mixture sufficiently to precipitate; and (c) isolating crystalline solid orlistat.

Preferably, steps (a) to (c) are repeated at least once to increase the purity of the crystalline solid orlistat.

The present invention provides the crystalline solid orlistat prepared in accordance with the process comprising the steps of:

(a) mixing orlistat in hexane to form a mixture at a first temperature;

(b) lowering the first temperature of the mixture sufficiently to precipitate; and (c) isolating crystalline solid orlistat.

The present invention provides a process of preparing a mixture of crystalline solid orlistat, or hydrate or solvate thereof, characterized by data selected from the group consisting of a XRD pattern with peaks at 5.8, 18.5, 19.5 and 22.3±0.2 degrees two-theta, a DSC melting endotherm at about 46.7° C., a XRD pattern with peaks at 4.8, 5.6, 14.9, 17.3, 19.2 and 22.0±0.2 degrees two-theta, and a DSC melting endotherm at about 46.6° C., comprising the steps of:

(a) dissolving orlistat in a solvent; and (b) inducing crystallization to obtain the mixture of crystalline solid orlistat.

Preferably, the solvent is at least one alcohol selected from the group consisting of methanol, ethanol, n-propanol, 1-propanol, 2-propanol, isopropanol, 1-butanol, i-butanol, sec-butanol, tert-butanol, N,N-dimethyl formamide, dimethyl sulfoxide, acetonitrile, acetone, ethyl acetate, isobutyl acetate, methyl isobutyl ketone, and acetic acid. Preferably, the solvent is an aliphatic hydrocarbon. More preferably, the aliphatic hydrocarbon is selected from the group consisting of hexane, pentane and heptane. Preferably, the solvent contains water. More preferably, the solvent is methanol. Most preferably, the mixture of methanol and water is present in a v/v ratio of about 1:0.3. Preferably, the solvent is a mixture of a first alcohol in combination with a second alcohol selected from the group consisting of methanol, ethanol, isopropanol, propanol, butanol, sec-butanol and t-butanol. Preferably, the crystallization step is induced by adding an anti-solvent or cooling.

The present invention provides the crystalline solid orlistat having a purity of at least about 95%. More preferably, the crystalline solid orlistat has a purity of at least about 98%.

The present invention provides a process of preparing orlistat, comprising the steps of:

a) preparing fermentation broth containing lipstatin;

b) extracting lipstatin from the fermentation broth;

c) hydrogenating the lipstatin to obtain orlistat; and d) separating the orlistat.

Preferably, the hydrogenating step c) is carried out in an organic solvent in the presence of a catalyst to obtain orlistat.

DETAILED DESCRIPTION OF THE INVENTION

Definitions:

As used herein, the term "lipstatin" refers to a precursor of orlistat. Orlistat, also known as tetrahydrolipstatin, has four more hydrogens than lipstatin.

As used herein, the term "under reduced pressure" refers to pressure which is less than 760 mm Hg. The term "vacuum" refers to pressure close to 0 mm Hg.

As used herein, the term "hydrogenation" refers to the catalytic addition of hydrogen to lipstatin with hydrogen gas in the presence of a catalyst; such catalyst includes palladium (Pd) or nickel (Ni).

As used herein, the term "XRD" refers to X-ray powder diffraction. One of skill in the art would appreciate that orlistat crystalline forms I or II possess unique XRD peaks provided herein.

As used herein, the term "bar" refers to 760 mm Hg. For example 1 bar refers to 760 mmHg and 2 bars refers to 2×760 mmHg.

The analysis of the samples was performed by HPLC, using RC C 18 type, 5 micron column. The mobile phase was a mixture of acetonitrile and 0.1% phosphoric acid in a vol/vol ratio of 8 to 2. Detection was done by UV detector at 205 nm wavelength.

Crystalline Solid Orlistat Form I

The present invention provides a crystalline solid orlistat, or hydrate or solvate thereof, characterized by data selected from the group consisting of a XRD pattern with peaks at 5.8, 18.5, 19.5 and 22.3±0.2 degrees two-theta and a DSC melting endotherm at about 46.7° C. Preferably, the crystalline solid orlistat is characterized by a XRD pattern with peaks at 5.8, 18.5, 19.5 and 22.3±0.2 degrees two-theta.

Figure 1:
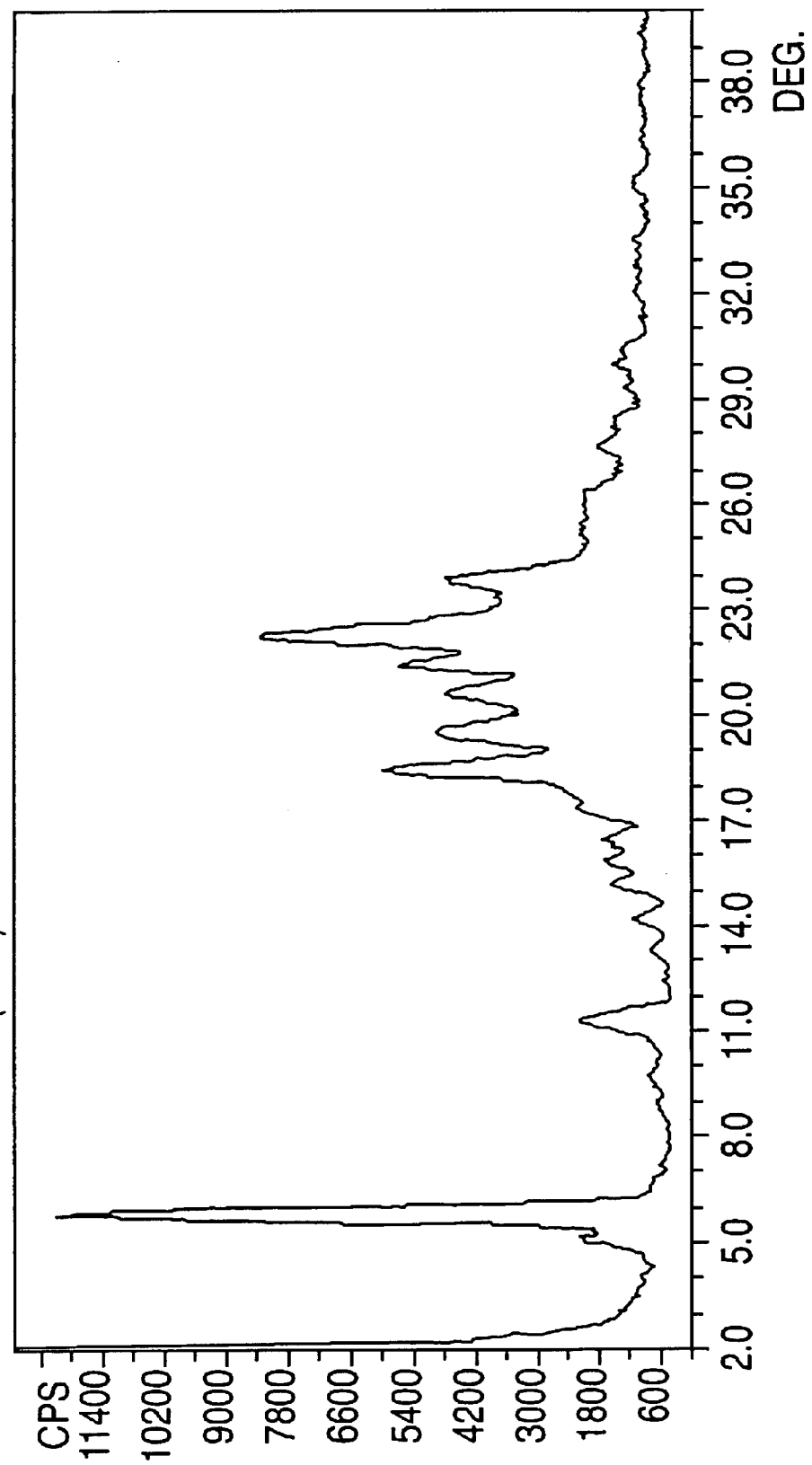
FIG. 1 represents the XRD diffractogram of crystalline solid orlistat form I.

Preferably, the crystalline solid orlistat is characterized by a XRD pattern substantially as depicted in FIG. 1.

Preferably, the crystalline solid orlistat characterized by a DSC melting endotherm at about 46.7° C.

Orlistat Crystalline Form II

The present invention provides a crystalline solid orlistat, or hydrate or solvate thereof, characterized by data selected from the group consisting of a XRD pattern with peaks at 4.8, 5.6, 14.9, 17.3, 19.2 and 22.0±0.2 degrees two-theta, a DSC melting endotherm at about 46.6° C.

Preferably, the crystalline solid orlistat is characterized by a XRD pattern with peaks at 4.8, 5.6, 14.9, 17.3, 19.2 and 22.0±0.2 degrees two-theta.

Figure 2:
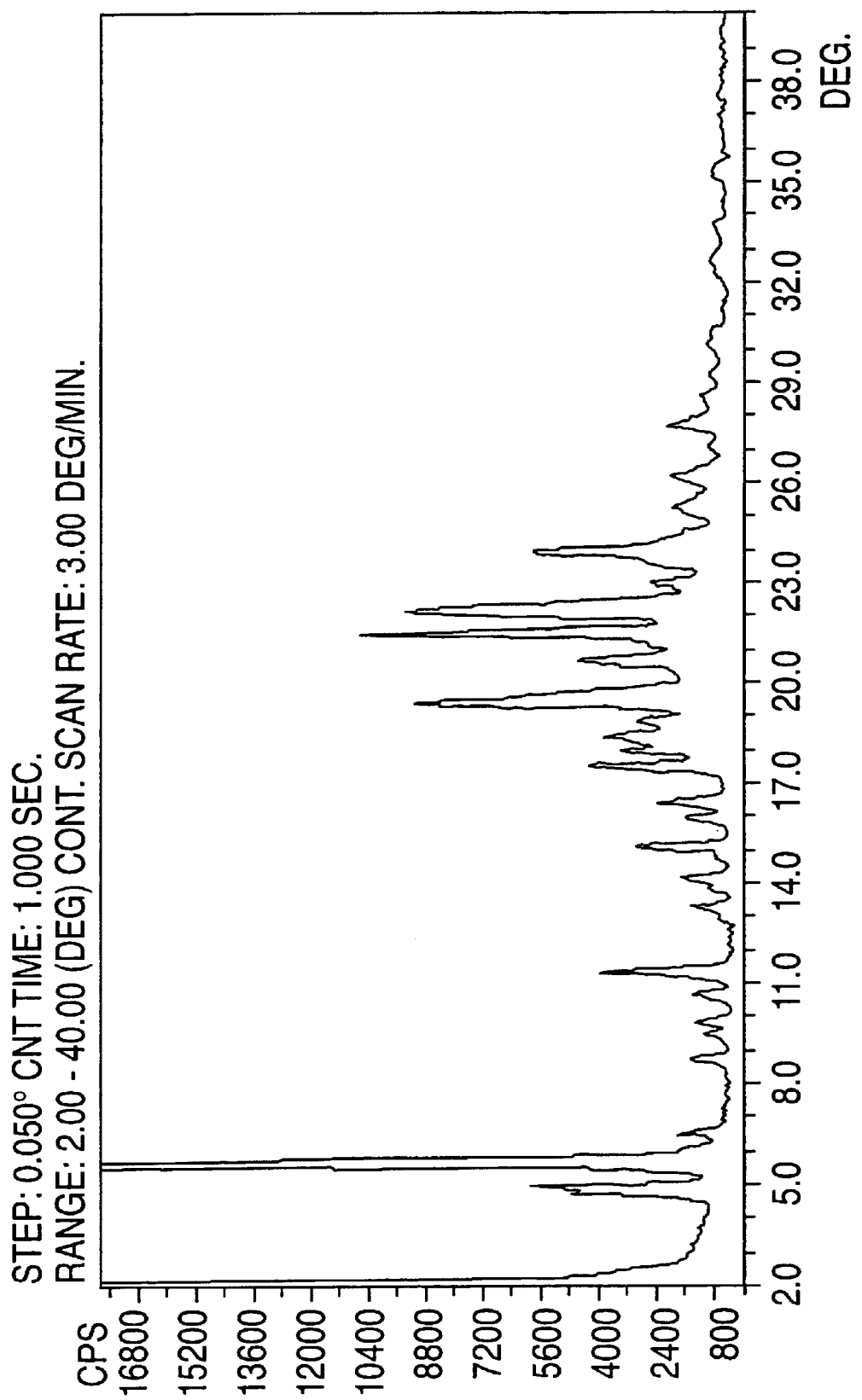
FIG. 2 represents the XRD diffractogram of crystalline solid orlistat form II.

Preferably, the crystalline solid orlistat is characterized by a XRD pattern substantially as depicted in FIG. 2.

Preferably, the crystalline solid orlistat is characterized by a DSC melting endotherm at about 46.6° C.

According to another embodiment, the present invention provides a process of preparing crystalline solid orlistat, or hydrate or solvate thereof, characterized by data selected from the group consisting of a XRD pattern with peaks at 5.8, 18.5, 19.5 and 22.3±0.2 degrees two-theta and a DSC melting endotherm at about 46.7° C., comprising the steps of:
  (a) dissolving orlistat in a solvent;
  (b) adding an anti-solvent or water to the solvent; and
  (c) isolating the crystalline solid orlistat.

Preferably, the solvent is a lower alkyl alcohol, acetone, acetonitrile, acetone, ethyl acetate, isobutyl acetate, methyl isobutyl ketone, and hexane. Preferably, the lower alkyl alcohol is selected from the group consisting of methanol, ethanol, n-propanol, and isopropanol.

Preferably, the anti-solvent is selected from the group consisting of hydrocarbon. More preferably, the hydrocarbon is selected from the group consisting of heptane, hexane, and cyclohexane. Most preferably, the solvent is methanol and the anti-solvent is hexane.

Preferably, the process steps of preparing a crystalline solid orlistat is repeated.

According to another embodiment, the present invention provides a process for preparing a crystalline solid form, or hydrate or solvate thereof, characterized by data selected from the group consisting of a XRD pattern with peaks at 4.8, 5.6, 14.9, 17.3, 19.2 and 22.0±0.2 degrees two-theta, a DSC melting endotherm at about 46.6° C., comprising the steps of:
  (a) mixing orlistat in hexane to form a mixture at a first temperature;
  (b) lowering the first temperature of the mixture sufficiently to precipitate; and
  (c) isolating crystalline solid orlistat.

According to another embodiment, the present invention further provides a process of preparing a mixture of crystalline solid orlistat forms, or hydrate or solvate thereof, characterized by data selected from the group consisting of a XRD pattern with peaks at 5.8, 18.5, 19.5 and 22.3±0.2 degrees two-theta, a DSC melting endotherm at about 46.7° C., a XRD pattern with peaks at 4.8, 5.6, 14.9, 17.3, 19.2 and 22.0±0.2 degrees two-theta, and a DSC melting endotherm at about 46.6° C., comprising the steps of:
  (a) dissolving orlistat in a solvent; and
  (b) inducing crystallization to obtain the mixture of crystalline solid orlistat.

Preferably, the solvent is selected from the group consisting of methanol, ethanol, n-propanol, 1-propanol, 2-propanol, isopropanol, 1-butanol, i-butanol, sec-butanol, tert-butanol, N,N-dimethyl formamide, dimethyl sulfoxide, acetonitrile, acetone, ethyl acetate, isobutyl acetate, methyl isobutyl ketone, and acetic acid. Preferably, the solvent is an aliphatic hydrocarbon. More preferably, the aliphatic hydrocarbon is selected from the group consisting of hexane, pentane and heptane.

Preferably, the solvent contains water. Preferably, the solvent is methanol. More preferably, the mixture of methanol and water is present in a v/v ratio of about 1:0.3.

Preferably, the solvent is a mixture of an alcohol in combination with another solvent selected from the group consisting of methanol, ethanol, isopropanol, propanol, butanol, sec-butanol and t-butanol.

Preferably, the crystallization step is induced by adding an anti-solvent or by cooling.

According to another embodiment, the present invention provides crystallized orlistat has a purity of at least about 95%. More preferably, the crystallized orlistat has a purity of at least about 98%.

According to another embodiment, the present invention provides a process for preparing novel crystalline forms of orlistat by crystallization. A preferred embodiment includes crystallization using a crystallization solution which is a mixture of a solvent and water. Preferably, the solvent comprises of methanol, ethanol, 1-propanol, 2-propanol, 1-butanol, i-butanol, tert-butanol, N,N-dimethyl formamide, dimethyl sulfoxide, acetonitrile, acetone or acetic acid. Preferably, a crystallization solution is a mixture of methanol and water in a volume-to-volume ratio of 1 mL (methanol) to 0.3 mL (water).

One of skill in the art would appreciate that some conditions for crystallization can be modified without affecting crystalline form of the orlistat obtained. For example, warming of the mixture may be necessary to completely dissolve the starting material. If warming does not clarify the mixture, the mixture can be diluted or filtered. To filter, the hot mixture can be passed through paper, glass fiber or other membrane material, or a clarifying agent such as celite. Depending upon the equipment used and the concentration and temperature of the solution, the filtration apparatus may need to be preheated to avoid premature crystallization.

The conditions can also be changed to induce precipitation. A preferred way of inducing precipitation is to reduce the solubility of the solute, for example, by cooling the solvent.

Alternatively, an anti-solvent may be added to a solution to decrease solubility of a particular compound, thus resulting in precipitation.

Another manner to accelerate crystallization is by seeding with a crystal of the product or scratching the inner surface of the crystallization vessel with a glass rod. Other times, crystallization can occur spontaneously without any inducement. The present invention covers both embodiments where precipitation is induced/accelerated or occurs spontaneously, except in the circumstance where the inducement/acceleration is critical for obtaining a particular crystalline form, e.g., the process requires the use of a particular anti-solvent.

It is appreciated that the present crystallization process can be repeated several times. The repetition of crystallization process will improve the purity of the crystalline orlistat. According to one embodiment, the present invention provides a process for hydrogenating lipstatin to obtain orlistat. Crude lipstatin can be used for the hydrogenation process to obtain orlistat. Other sources including commercially available sources of lipstatin can also be used. Preferably, crystalline lipstatin is used for the hydrogenation.

According to another embodiment, Pd (palladium) or Ni (nickel) catalysts can be used. Hydrogenation is performed at an reaction pressure not greater than 5 bar (i.e., 5 times atmospheric pressure (760 mmHg)). The preferred reaction pressure is about 1–3 bar. The most preferred reaction pressure is about atmospheric pressure (760 mmHg). The preferred reaction temperature is about 10 to about 50° C. The preferred solvents are acetonitrile and alcohols. The most preferred solvents are methanol and acetone.

The present invention is described in further detail with reference to the following examples. However, the scope of the present invention is by no means restricted by these specific examples.

EXAMPLES

Example 1

A fermentation broth (3.4 kg) containing lipstatin was extracted with i-butyl acetate at a pH of about 2.0–10.5. The extraction achieved a yield of 94%.

The i-butyl acetate phase was further washed with water at a pH of about 3.0–8.0.

The washed i-butyl acetate phase was concentrated in a vacuum at a maximum temperature of about 80° C. The concentrated i-butyl acetate phase (311.9 grams) contained the lipstatin (1.305 gram) and was then extracted three times with methanol. The methanol phases were combined. The combined methanol phase contained 1.100 gram of lipstatin. The overall yield of the steps was 79%.

Example 2

A methanol phase was produced according to Example 1.

The methanol phase (936 mL) was concentrated under reduced pressure to an oily residue (20.39 grams). The oily residue was diluted with acetonitrile (125 mL). The diluted solution contained the lipstatin (1.100 gram).

The acetonitrile solution was extracted three times with hexane. The hexane phases were combined (300 mL) and washed three times with acetonitrile (10 mL). The acetonitrile phases were combined. The combined acetonitrile phases contained the lipstatin (952 mg). The solution was concentrated in vacuum at a maximum temperature of 60° C. The mass of concentrate was 4.95 grams. The yield of this step was 87%.

Example 3

An acetonitrile concentrate was produced according to Example 2.

The concentrate (4.95 grams) was diluted with a methanol:water (70:15) mixture (85 mL) resulting in a diluted solution containing lipstatin. The diluted solution containing lipstatin (952 mg) was extracted five times with hexane (85 mL). The hexane phases were combined and concentrated in vacuum at a maximum temperature of about 60° C. to a volume of 85 mL.

The concentrated hexane solution was extracted five times with methanol:water (70:15) mixture (85 mL). The combined methanol:water phase was concentrated in vacuum at a maximum temperature of about 80° C. to an oily residue (1.267 gram). The oily residue contained lipstatin (748 mg). The yield of this step was 86%.

Example 4

An oily residue was produced according to Example 3.

The oily residue (603 mg) was diluted with methanol (10 mL). The diluted solution contained lipstatin (356 mg) and was passed through an anion-exchanger (15 mL). The type of anion-exchanger used was Amberlite™ IRA 67 resin in hydroxide form. The resin was washed with methanol. Fractions containing lipstatin were collected. The volume of the combined fractions was 20 mL. The combined fractions contained about 302 mg lipstatin and about 142 mg other substances.

Example 5

A lipstatin containing 302 mg active substance was produced according to Example 4.

The lipstatin was hydrogenated in the presence of a catalyst in a methanol solution. The hydrogenation of about 302 mg lipstatin resulted in about 270 mg orlistat (tetrahydrolipstatin).

The present invention of orlistat crystallization will now be further explained in the following examples. These examples should not be construed as limiting to the invention.

X-Ray Diffraction Method:

Conditions for obtaining powder x-ray diffraction (XRD) patterns: The powder x-ray diffraction patterns were obtained by methods known in the art using a Philips x-ray powder diffractometer, Phillips Generator TW 1830; Goniometer PW 3020; MPD Control PW 3710; X-Ray tube with Cu target anode; Monochromator proportional counter; Divergence slits 1°, Receiving slit 0.2 mm, Scatter slit 1°; 40 KV, 30 mA; and Scanning speed step 0.05 degrees to 2 degrees/min.

Example 6

Orlistat (270 mg) was crystallized from methanol (1 mL) by adding water (200 microlitres) after cooling at a temperature of about 0–10° C. for at least 10 hours. Crystals were filtered and dried. Crystallization resulted in orlistat (160 mg). The purity was 80%. The purity of orlistat was increased to 95% and further 98% further crystallization.

Example 7

Orlistat (produced according to Examples 5 (160 mg)) was crystallized from hexane (1.6 mL) after cooling at a temperature of about 0–10° C. for at least 10 hours. Crystals were filtered and dried. The crystallization resulted in orlistat (105.7 mg). The purity was about 89%. The purity of orlistat was increased to 95% and further 98% further crystallization.

Example 8

0.7 gram orlistat was dissolved in 0.7 mL ethanol. Hexane of 0.7 mL was added to the solution. It was dried at 20–25° C. for 24 hours. It was further dried at 38° C. for 48 hours without any filtration (sample number 1–1).

Example 9

0.7 gram orlistat was dissolved in 1.0 mL acetonitrile. Water of 0.3 mL was added to the solution. It was dried at 20–25° C. for 24 hours. It was further dried at 38° C. for 48 hours without any filtration (sample number 2).

Example 10

0.7 gram orlistat was dissolved in 0.7 mL acetonitrile. Hexane of 0.7 mL was added to the solution. It was dried at 20–25° C. for 24 hours. It was further dried at 38° C. for 48 hours without any filtration (sample number 2-1).

Example 11

0.7 gram orlistat was dissolved in 0.7 mL n-Propanol. Hexane of 0.7 mL was added to the solution. It was dried at 20–25° C. for 24 hours. It was further dried at 38° C. for 48 hours without any filtration (sample number 3-1).

Example 12

0.7 gram orlistat was dissolved in 1.0 mL isopropanol. Water of 0.3 mL was added to the solution. It was dried at 20–25° C. for 24 hours. It was further dried at 38° C. for 48 hours without any filtration (sample number 4).

Example 13

0.7 gram orlistat was dissolved in 0.7 mL isopropanol. Hexane of 0.7 mL was added to the solution. It was dried at 20–25° C. for 24 hours. It was further dried at 38° C. for 48 hours without any filtration (sample number 4-1).

Example 14

0.7 gram orlistat was dissolved in 1.0 mL acetone. Water of 0.3 mL was added to the solution. It was dried at 20–25° C. for 24 hours. It was further fried at 38° C. for 48 hours without any filtration (sample number 5).

Example 15

0.7 gram orlistat was dissolved in 0.7 mL acetone. Hexane of 0.7 mL was added to the solution. It was dried at 20–25° C. for 24 hours. It was further dried at 38° C. for 48 hours without any filtration (sample number 5-1).

Example 16

0.7 gram orlistat was dissolved in 0.7 mL ethyl acetate. Hexane of 0.7 mL was added to the solution. It was dried at 20–25° C. for 24 hours. It was further dried at 38° C. for 48 hours without any filtration (sample number 8-1).

Example 17

0.7 gram olistat was dissolved in 0.7 mL isobutyl acetate. Hexane of 0.7 mL was added to the solution. It was dried at 20–25° C. for 24 hours. It was further dried at 38° C. for 48 hours without any filtration (sample number 9-1).

Example 18

0.7 gram orlistat was dissolved in 0.7 mL methyl isobutyl ketone. Hexane of 0.7 mL was added to the solution. It was dried at 20–25° C. for 24 hours. It was further dried at 38° C. for 48 hours without any filtration (sample number 10-1).

Example 19

0.7 gram orlistat was dissolved in 0.7 mL methanol. Hexane of 0.7 mL was added to the solution. It was dried at 20–25° C. for 24 hours. It was further dried at 38° C. for 48 hours without any filtration (sample number 13-1).

Example 20

0.7 gram orlistat was dissolved in 0.7 mL methanol. Water of 0.3 mL was added to the solution. It was cooled at 0–5° C. for 1 hour. Filtered crystals were dried at 20–25° C. for 1 hour and at 38° C. for 1 hour (sample number 14-1).

Example 21

0.7 gram orlistat was dissolved in 7.0 mL hexane. Crystals were filtered after 20 hours cooling at 0–5° C. Drying was carried out at 20–25° C. for 1 hour and at 38° C. for 1 hour (sample number 16).

Example 22

The melting points (DSC) and enthapy of the following orlistat samples were measured and presented in the following table. The crystalline forms (XRD) of the orlistat samples were also presented.

| Sample Numbers | melting endotherm ° C. (DSC) | enthapy ($\Delta$) (J/gram) | Crystalline forms (XRD) |
| --- | --- | --- | --- |
| 1-1 | 46.3 | 87 | I > II |
| 2 | 47.0 | 92 | I > II |
| 2-1 | 47.1 | 85 | I > II |
| 3-1 | 46.7 | 87 | I > II |
| 4 | 46.5 | 91 | I > II |
| 4-1 | 46.8 | 92 | I > II |
| 5 | 46.2 | 90 | I > II |
| 5-1 | 46.9 | 90 | I > II |
| 8-1 | 46.9 | 93 | I > II |
| 9-1 | 46.5 | 85 | I > II |
| 10-1 | 46.5 | 88 | I > II |
| 13-1 | 46.7 | 91 | I |
| 14-1 | 46.2 | 90 | I > II |
| 16 | 46.6 | 93 | II |

">" refers to "substantially excess". For example "I > II" means that form I is in substantially excess amount than form II.

One of ordinary skill in the art would appreciate that the experimental conditions require optimization in order to crystallize and obtain further purified crystalline orlistat.

Pharmaceutical Formulations of Orlistat Crystalline Forms:

Orlistat crystalline forms I and II are useful for treating obesity. They can be formulated into a variety of compositions for administration to a mammal including humans and animals.

Pharmaceutical compositions of the present invention contain orlistat crystalline form I or orlistat crystalline form II. In addition to the active ingredient(s), the pharmaceutical compositions of the present invention can contain one or more excipients. Excipients are added to the composition for a variety of purposes. Diluents increase the bulk of a solid pharmaceutical composition and can make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet can include excipients whose functions include helping to bind the active ingredient and other excipients together after compression. Binders for solid pharmaceutical compositions include for example acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach can be increased by the addition of a disintegrant to the composition. Disintegrants include for example alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of non-compacted solid composition and improve the accuracy of dosing. Excipients that can function as glidants include for example colloidal silicon dixoide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that can be included in the composition of the present invention include for example maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Orlistat crystalline form I or II, and any other solid excipients are dissolved or suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity enhancing agent to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. The dosages can be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs.

A dosage form of the present invention is a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filing can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosure of which are incorporated by reference in their entireties.

What is claimed is:

1. A crystalline solid orlistat, or hydrate or solvate thereof, characterized by data selected from the group consisting of a XRD pattern with peaks at 5.8, 18.5, 19.5 and 22.3±0.2 degrees two-theta and a DSC melting endotherm at about 46.7° C.

2. The crystalline solid orlistat of claim 1, wherein the crystalline solid orlistat is characterized by the XRD pattern with peaks at 5.8, 18.5, 19.5 and 22.3±0.2 degrees two-theta.

3. The crystalline solid orlistat of claim 2, wherein the crystalline solid orlistat is further characterized by a XRD pattern substantially as depicted in FIG. 1.

4. The crystalline solid orlistat of claim 1, wherein the crystalline solid orlistat is characterized by the DSC melting endotherm at about 46.7° C.

5. A crystalline solid orlistat, or hydrate or solvate thereof, characterized by data selected from the group consisting of a XRD pattern with peaks at 4.8, 5.6, 14.9, 17.3, 19.2 and 22.0±0.2 degrees two-theta, and a DSC melting endotherm at about 46.6° C.

6. The crystalline solid orlistat of claim 5, wherein the crystalline solid orlistat is characterized by the XRD pattern with peaks at 4.8, 5.6, 14.9, 17.3, 19.2 and 22.0±0.2 degrees two-theta.

7. The crystalline solid orlistat of claim 6, wherein the crystalline solid orlistat is further characterized by a XRD pattern substantially as depicted in FIG. 2.

8. The crystalline solid orlistat of claim 5, wherein the crystalline solid orlistat is characterized by a DSC melting endotherm at about 46.6° C.

9. A process of preparing crystalline solid orlistat, or hydrate or solvate thereof, characterized by data selected from the group consisting of a XRD pattern with peaks at 5.8, 18.5, 19.5 and 22.3±0.2 degrees two-theta and a DSC melting endotherm at about 46.7° C., comprising the steps of:

(a) dissolving orlistat in a solvent;

(b) adding an anti-solvent or water to the solvent; and (c) isolating the crystalline solid orlistat.

10. The process of claim 9, wherein the solvent is a lower alkyl alcohol, acetone, acetonitrile, acetone, ethyl acetate, isobutyl acetate, methyl isobutyl ketone, and hexane.

11. The process of claim 10, wherein the lower alkyl alcohol is selected from the group consisting of methanol, ethanol, n-propanol, and isopropanol.

12. The process of claim 9, wherein the anti-solvent is a hydrocarbon.

13. The process of claim 12, wherein the hydrocarbon is selected from the group consisting of hexane, cyclohexane and heptane.

14. The process of claim 9, wherein the solvent is methanol and the anti-solvent is hexane.

15. The process of claim 9, wherein the steps (a) to (c) are repeated at least once to increase the purity of the crystalline solid orlistat.

16. The crystalline solid orlistat prepared in accordance with the process of claim 9.

17. The crystalline solid orlistat of claim 16, wherein the crystalline solid orlistat is characterized by a XRD pattern with peaks at 5.8, 18.5, 19.5 and 22.3±0.2 degrees two-theta.

18. The crystalline solid orlistat of claim 17, wherein the crystalline solid orlistat is further characterized by a XRD pattern substantially as depicted in FIG. 1.

19. The crystalline solid orlistat of claim 16, wherein the crystalline solid orlistat is characterized by a DSC melting endotherm at about 46.7° C.

20. A process for preparing a crystalline solid orlistat, or hydrate or solvate thereof, characterized by data selected from the group consisting of a XRD pattern with peaks at 4.8, 5.6, 14.9, 17.3, 19.2 and 22.0±0.2 degrees two-theta, and a DSC melting endotherm at about 46.6° C., comprising the steps of:

(a) mixing orlistat in hexane to form a mixture at a first temperature;

(b) lowering the first temperature of the mixture sufficiently to precipitate; and (c) isolating crystalline solid orlistat.

21. The process of claim 20, wherein the steps (a) to (c) are repeated at least once to increase the purity of the crystalline solid orlistat.

22. The crystalline solid orlistat prepared in accordance with the process of claim 20.

23. The crystalline solid orlistat of claim 22, wherein the crystalline solid orlistat is characterized by the XRD pattern with peaks at 4.8, 5.6, 14.9, 17.3, 19.2 and 22.0±0.2 degrees two-theta.

24. The crystalline solid orlistat of claim 23, wherein the crystalline solid orlistat is further characterized by a XRD pattern substantially as depicted in FIG. 2.

25. The crystalline solid orlistat of claim 22, wherein the crystalline solid orlistat is characterized by the DSC melting endotherm at about 46.6° C.

26. A process of preparing a mixture of crystalline solid orlistat, or hydrate or solvate thereof, characterized by data selected from the group consisting of a XRD pattern with peaks at 5.8, 18.5, 19.5 and 22.3±0.2 degrees two-theta, a DSC melting endotherm at about 46.7° C., a XRD pattern with peaks at 4.8, 5.6, 14.9, 17.3, 19.2 and 22.0±0.2 degrees two-theta, and a DSC melting endotherm at about 46.6° C., comprising the steps of:

(a) dissolving orlistat in a solvent; and (b) inducing crystallization to obtain the mixture of crystalline solid orlistat.

27. The process of claim 26, wherein the solvent is at least one alcohol selected from the group consisting of methanol, ethanol, n-propanol, 1-propanol, 2-propanol, isopropanol, 1-butanol, i-butanol, sec-butanol, tert-butanol, N,N-dimethyl formamide, dimethyl sulfoxide, acetonitrile, acetone, ethyl acetate, isobutyl acetate, methyl isobutyl ketone, and acetic acid.

28. The process of claim 26, wherein solvent is an aliphatic hydrocarbon.

29. The process of claim 28, wherein the aliphatic hydrocarbon is selected from the group consisting of hexane, pentane and heptane.

30. The process of claim 26, wherein the solvent contains water.

31. The process of claim 26, wherein the solvent is methanol.

32. The process of claim 26, wherein the mixture of methanol and water is present in a v/v ratio of about 1:0.3.

33. The process of claim 27, wherein the solvent is a mixture of a first alcohol in combination with a second alcohol selected from the group consisting of methanol, ethanol, isopropanol, propanol, butanol, sec-butanol and t-butanol.

34. The process of claim 26, wherein the crystallization step is induced by adding an anti-solvent.

35. The process of claim 26, wherein the crystallization step is induced by cooling.

36. The crystalline solid orlistat as prepared by the process of one of claims 9, 20, and 26, wherein the crystalline solid orlistat has a purity of at least about 95%.

37. The crystalline solid orlistat as prepared by the process of one of claims 9, 20 and 26, wherein the crystalline solid orlistat has a purity of at least about 98%.

* * * * *

(12) EX PARTE REEXAMINATION CERTIFICATE (7806th)
United States Patent
Keri et al.

(10) Number: US 6,734,314 C1
(45) Certificate Issued: Oct. 12, 2010

(54) PREPARATION OF ORLISTAT AND ORLISTAT CRYSTALLINE FORMS

(75) Inventors: Vilmos Keri, Debrecen (HU); Andrea Csorvasi, Debrecen (HU); Judith Aronhime, Rehovot, IL (US)

(73) Assignee: Biogal Gyogyszergyar RT, Debrecen (HU)

Reexamination Request:
No. 90/009,494, Jun. 17, 2009

Reexamination Certificate for:
Patent No.: 6,734,314
Issued: May 11, 2004
Appl. No.: 10/313,601
Filed: Dec. 4, 2002

Related U.S. Application Data

(60) Provisional application No. 60/337,218, filed on Dec. 4, 2001.

(51) Int. Cl.
*C07D 305/00* (2006.01)
*C07D 305/12* (2006.01)
*C12P 17/02* (2006.01)

(52) U.S. Cl. .................. 549/328; 549/263; 435/123

(58) Field of Classification Search .................. None
See application file for complete search history.

(56) References Cited

U.S. PATENT DOCUMENTS 4,598,089 A 7/1986 Hadvary et al.
5,314,506 A * 5/1994 Midler et al. ............. 23/295 R

FOREIGN PATENT DOCUMENTS

EP 1028115 8/2000

OTHER PUBLICATIONS

Barbier P., et al., "129. Stereoselective Syntheses of Tetrahydrolipstatin and of an Analogue, Potent Pancreatic–Lipase Inhibitors Containing a β–Lactone Moiety," Helvetica Chimica Acta, vol. 70 (1987) 1412–1418.

* cited by examiner

*Primary Examiner*—Dwayne C Jones

(57) ABSTRACT

The present invention is directed to a process of converting lipstain to orlistat by catalytic hydrogenation. The present invention further discloses novel crystalline solid orlistat forms, designated form I and form II and methods for their preparation.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-37 are cancelled.

* * * * *